United States Patent [19]

Rhodes

[11] Patent Number: 5,631,423
[45] Date of Patent: May 20, 1997

[54] METHOD FOR RESONANT MEASUREMENT

[75] Inventor: George W. Rhodes, Albuquerque, N.M.

[73] Assignee: Quatro Corporation, Albuquerque, N.M.

[21] Appl. No.: 409,218

[22] Filed: Mar. 25, 1995

[51] Int. Cl.$^6$ .................................................. G01H 13/00
[52] U.S. Cl. ................................................ 73/579; 73/602
[58] Field of Search ......................... 73/579, 602, 12.02, 73/630, 593, 645, 646, 659; 364/508; 310/336

[56] References Cited

U.S. PATENT DOCUMENTS

| | | | |
|---|---|---|---|
| 4,428,235 | 1/1984 | Sugiyama | 73/602 |
| 5,257,544 | 11/1993 | Khuri-Yakub | 73/579 |
| 5,355,731 | 10/1994 | Dixon | 73/579 |

*Primary Examiner*—Christine K. Oda
*Attorney, Agent, or Firm*—Ronald R. Snider

[57] ABSTRACT

A method of measurement of objects by resonant ultra sound is used to determine object surface to near surface flaws. First, the frequency for expected degenerate surface acoustic wave responses is determined for one or more input frequencies and then splitting of degenerate resonant modes are observed to identify the presence of surface flaws in the object.

15 Claims, 4 Drawing Sheets

METHOD FOR RESONANT MEASUREMENT

BACKGROUND OF INVENTION

1. Field of the Invention

This invention relates to nondestructive testing and, more particularly, to nondestructive detection of surface flaws in objects. A flaw may be a chip, fingerprint, scratch, pit, or any other deviation from a smooth surface. This invention specifically relates to measurement of surface flaws in spherical objects such as ball bearings.

2. The Prior Art

Computational procedures have been developed to find the mechanical resonances of objects other than a sphere but which also have some symmetries. This work is described in "On the modes of free vibrations on inhomogeneous and anisotropic elastic objects" by Visscher et al., J. Acoust Soc. Am., 90 (4) p. 2154, 1991. Examples are, objects, such as a cylinder, rectangular parallel piped, cone, ellipsoid, or pyramids with regular polygon bases.

Testing of objects by use of sound (including ultrasound) and vibrations is well known. The prior art is extensive and encompasses many types of non-destructive testing. Resonant sound and ultrasound has also been used for testing purposes as described in U.S. Pat. Nos. 5,062,296, 4,976, 148, and 5,355,731 which are incorporated herein by reference, except for their incorporation by reference of other information.

Also incorporated herein by reference is U.S. patent application Ser. No. 08/075,210 entitled Ultrasonic Differential Measurement filed Jun. 10, 1993, now U.S. Pat. No. 5,408,880. Applicant does not incorporate into this application any material which was incorporated into these prior patent applications by reference.

In U.S. Pat. No. 5,355,731 entitled, "Sphericity Determination Using Resonant Ultrasound Spectroscopy," there is described a method of analysis which is specific to sphericity determination. One mode of employment of RUS relates the resonant ultrasound spectrum of a component to the dimensions and material properties of the components.

SUMMARY OF THE INVENTION

This invention relates to a method of determination of flaws in or on the surface of an object. The flaws may be in the form of surface cracks, pits, finger prints, chips, scratches, or other surface imperfections of the object or any other surface physical characteristics which would degenerate resonant frequencies. In the method of this invention, the existence and frequencies of degenerate resonant vibrational modes which are dependent only upon surface acoustic waves (SAW) are first calculated or predicted by means of a mathematical analysis of the object to be tested. The object is then examined by exciting it with a mechanical transducer such that the excitation frequency is slowly varied from one predetermined frequency to another. From the prediction, modes are identified that should be degenerate (i.e. several modes will vibrate at precisely the same frequency) in an unflawed object. If flaws exist, the degenerate modes are distorted by spreading change of shape, noise like vibrations at many frequencies, resonance at a plurality of different frequencies, or other deviations from the predicted resonance of a substantially perfect object resolved (or split) into two or more closely spaced resonances. Objects exhibiting deviation from predicted resonance characteristics are identified as flawed or defective.

To achieve the foregoing and other objects, and in accordance with the purposes of the present invention, as embodied and broadly described herein, the process of this invention is a method for testing the surface of objects based on their vibrational response. To achieve this, a vibrational (sound) spectrum at a acoustic wave frequency (SAW) is mathematically generated for an object, and the object is also measured. Comparison of the two enables detection of defective objects.

The detection of the flaws described above is addressed by the present invention and a resonant ultrasound spectroscopy (RUS) technique is presented for examining all of the objects made in a production run. It is therefore an object of the present invention to provide for inspecting objects at rates consistent with a manufacturing process.

A further object of the present invention is to provide an object inspection process that characterizes the entire body regardless of orientation in an inspection device.

It is another object of the present invention to provide an inspection technique that provides high sensitivity to surface flaws.

It is a further object of this invention to provide a method for testing for surface flaws of spherical objects such as bearing balls. More specifically, ceramic $Si_3N_4$ (silicon nitride) bearing balls can be tested for surface defects while internal defects are not detected.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

In this invention, applicant provides an improvement by selecting the frequency of resonant testing to include resonant modes which are dependent solely upon surface acoustic waves. The use of surface acoustic wave resonant frequencies allows testing of the object which will exclude deviations, variances, or other differences beneath the surface, such as voids, cavities, or internal cracks. The testing is therefore a selective testing method which tests only for surface conditions, and which excludes characteristics of the object under test.

Ceramic components made from $Si_3N_4$ (silicon nitride) have shown great promise in aerospace applications. $Si_3N_4$ weighs about one third as much as steel and is almost as hard as diamond. Since $Si_3N_4$ components can operate from cryogenic to very elevated ($\geq 800°$ C.) temperatures, in corrosive environments and under great loads, they promise increased performance in certain applications. Destructive materials testing has shown that $Si_3N_4$ components almost always have a defect near the center of the part. That kind of defect rarely effects the part's performance since only the materials characteristics of the outer regions matter. Tribological testing has shown that only defects within 2 mm of the surface, on a ½ inch $Si_3N_4$ sphere, effect the part's durability. Normal Resonance Inspection testing examines the bulk object for all defects. Unless a sphere is homogeneous and isotropic, this bulk inspection will yield an indication of a defect and have no way to differentiate between deeply buried flaws, which don't matter versus those which are surface/near surface, which do.

In U.S. Pat. No. 5,355,731, it was demonstrated that spherical objects exhibit degenerate resonant modes. If the spherical symmetry is broken by a flaw, crack, or subsurface defect, the degeneracy is such that what appeared to be a single resonance becomes split into several distinct resonances. This splitting is used quantitatively to determine errors in sphericity, while the resonances themselves are used to determine density, diameter or elastic moduli depending on which two of these three quantities are known. This disclosure does not identify any method for testing for surface distortion by scratches, fingerprints, etc, while excluding internal degenerate features.

It is known that surface acoustic waves occur in spherical shaped objects in accordance with the following conditions:

The general equation for a Rayleigh/Surface Accoustic wave on a plane of infinite extent is given by:

$$\frac{\partial^2 u}{\partial t^2} - c^2 \Delta u = 0 \qquad \text{Equation 1}$$

where u is the displacement vector of a point: on the plane. This is described in "Theory of Elasticity", 3rd. Edition, Landau and Lifshitz, Course of Theoretical Physics, 7 Pergamon Press 1986 which is incorporated herein by reference. In equation 1, t is the time and c is the corresponding velocity of sound. When this equation is converted to the spherical coordinates appropriate for a sphere the following equation is obtained.

$$\frac{\partial^2 u(r,\theta,\phi,t)}{\partial t^2} = c^2 \left[ \frac{1}{r^2} \frac{\partial}{\partial r} \left( r^2 \frac{\partial u}{\partial r} \right) + \frac{1}{r^2 \sin\theta} \frac{\partial}{\partial \theta} \left( \sin\theta \frac{\partial u}{\partial \theta} \right) + \frac{1}{r^2 \sin^2\theta} + \frac{\partial^2 u}{\partial \phi^2} \right]$$

Equation 2

First the displacements are calculated for every mode as a function of the radius of the sphere. If the displacement decreases rapidly with radius, a surface accoustic wave is identified.

BRIEF DESCRIPTION OF THE DRAWINGS

The accompanying drawings, which are incorporated in and form a part of the specification, illustrate an embodiment of the present invention and, together with the description, serve to explain the principles of the invention.

FIG. 3b shows the effect of a fingerprint on a near perfect ball depicted in 3a.

DETAILED DESCRIPTION OF THE INVENTION

In accordance with the present invention resonant ultrasound spectroscopy (RUS) provides a rapid and accurate method for determining object deviations from specifications. A new technique for using RUS is provided. Quick inspection of objects determines their acceptability from the quality acceptance standpoint. Inspection is possible for certain objects too difficult to inspect by any other means at rates consistent with operation of a typical production line. Thus, product quality is assured, not estimated, and production manufacturing trends can be identified and corrected before quantities of defective products are manufactured.

Figure 1:
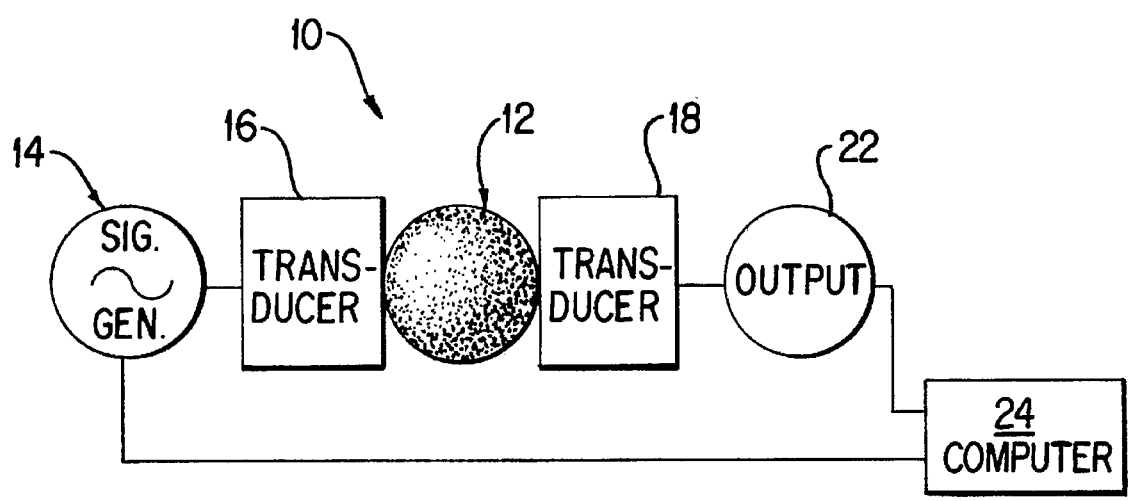
FIG. 1 shows a block diagram of a testing apparatus in accordance of this invention.

FIG. 1 depicts a simplified schematic of a system 10 for generating and analyzing the RUS spectrum of a spherical object 12. The object geometry may be any one where surface acoustic wave response can be mathematically described. Signal generator 14 excites transducer 16 for vibrating ball 12 over a predetermined frequency range, e.g., between 4 and 4000 Khz. The response of cone 12 is detected by transducer 18 and supplied to an output amplifier 22. A suitable RUS system 10 is described in U.S. Pat. No. 4,976,148, issued Dec. 11, 1990, to Migliori, et al. (incorporated herein by reference, except for parts incorporated by reference into '148). The outputs from amplifier 22 are input to computer 24 for analysis and computation of the difference between the sphere 12 resonant vibrational modes and those of a perfect sphere.

Figure 2:
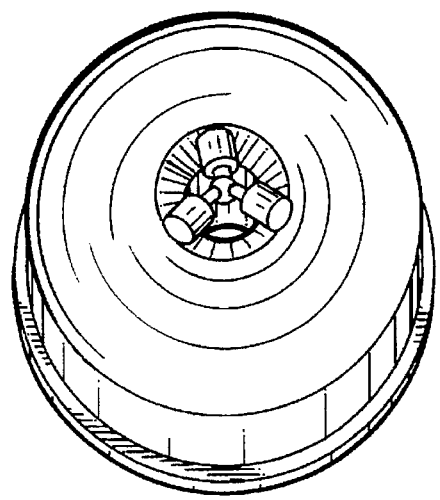
FIG. 2 shows a ball object supported on 3 transducers.

FIG. 2 shows a ball supported by three separate transducers. In this embodiment, any single transducer can be used for an input transducer and any of the remaining two transducers can be used for the receiving transducer. For purposes of this invention, it is not necessary to receive on two or more transducers, but it is within the scope of the invention to receive on a plurality of transducers.

In an overview of the present method, RUS spectra for the vibrational modes of a perfect object are computed as a function of shear modulus and Poisson's ratio. A RUS spectrum is obtained from a production object and components of the spectrum, i.e., the degenerate resonant modes, are identified from the perfect object surface acoustic wave calculations. The degenerate modes for a sphere surface are determined as described in the description of equations 1 and 2 above.

When an object surface deviates from perfect, at least some of the degenerate resonant frequencies become spaced or distorted.

Other nonuniformities in the manufactured object such as cracks or internal voids will also affect the RUS spectrum such that a defective object can be detected. However, it is an object of this invention to test at frequencies which can detect surface changes and exclude response to internal structural voids, cracks, or other deviations from a substantially perfect object.

The apparatus of the current invention comprises the ultrasonic resonant spectroscopy and transducers for measuring resonances of the test object. The transducer stage, with three transducers mounted approximately 120° apart, supports the test object (ball) for the resonance test. Solutions of the wave equation, for a sphere, reveal some modes which are unique for surface acoustic waves (SAW). These SAW resonances have the special property of traveling around the surface with a penetration depth limit of approximately one wavelength of the resonant frequency. This computes a value of 2.5 mm penetration depth if the material has a SAW resonance at 2 Mhz and the velocity of sound in the material is 5 km/second. Computations performed on a Los Alamos National Laboratory CRAY computer show that the SAW properties exist only for modes which are mixed rather than either pure shear or longitudinal waves. These SAW resonances always exhibit very high symmetry numbers and are at least 31 fold degenerate. Those selected for examples here exhibit 37 fold symmetry. This predicts that a seriously flawed sample should display 37 discernable peaks where a perfect surface would indicate but a single peak. Examples of these measurements are shown in FIGS.

Figure 3A:
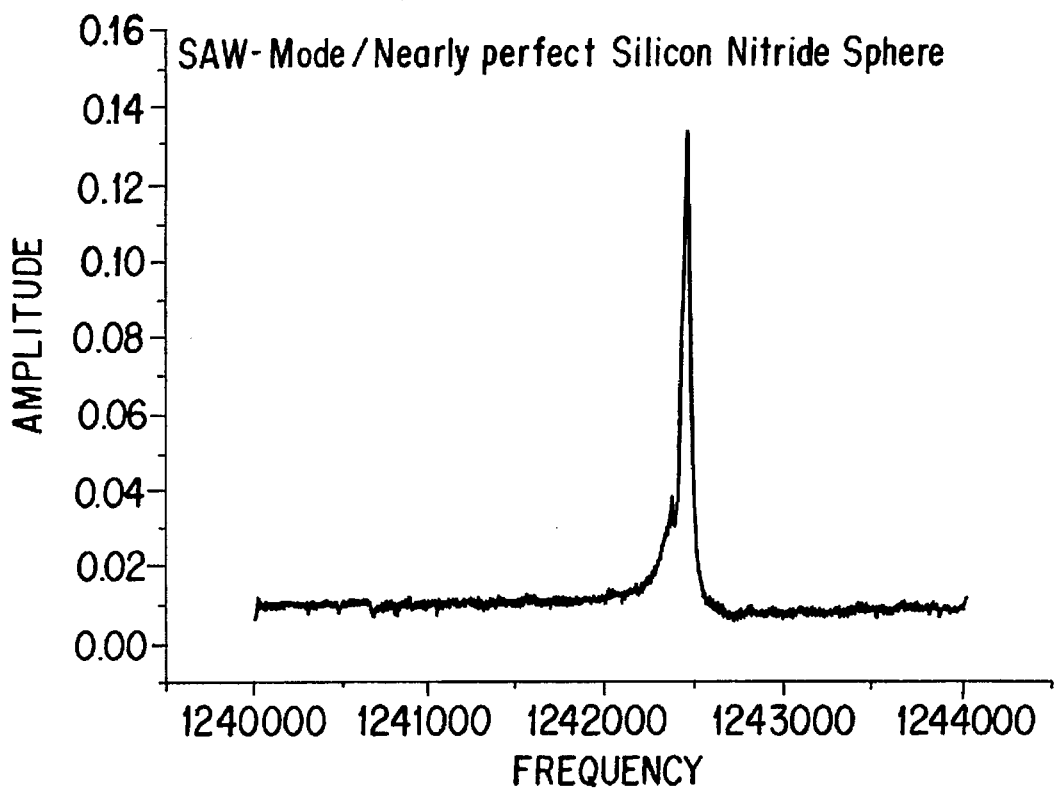
FIG. 3a shows a near perfect ball subjected to RUS at a surface acoustic wave frequency.
Figure 3B:
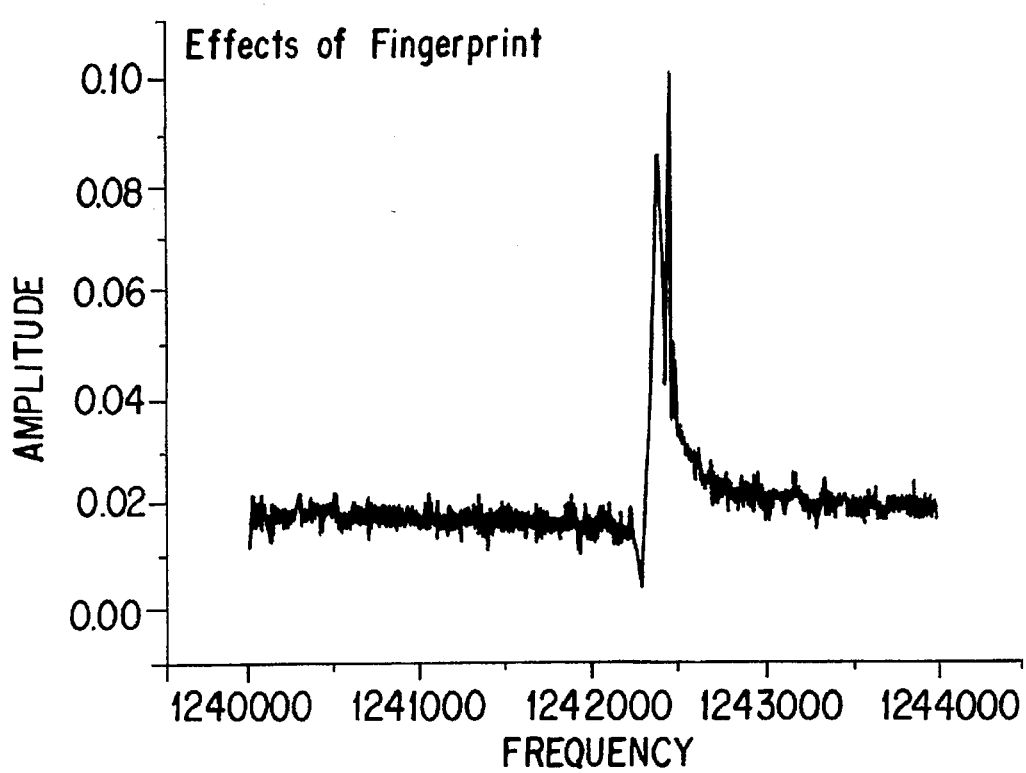

3a to 3e. Several samples, containing different flaws, were measured at the requisite mode. FIG. 3a illustrates a nearly perfect ball surface. FIG. 3b shows the effect of a single fingerprint on the same ball. Thus it is imperative that these samples be handled in a clean environment in order to obtain a useful measurement.

Figure 3C:
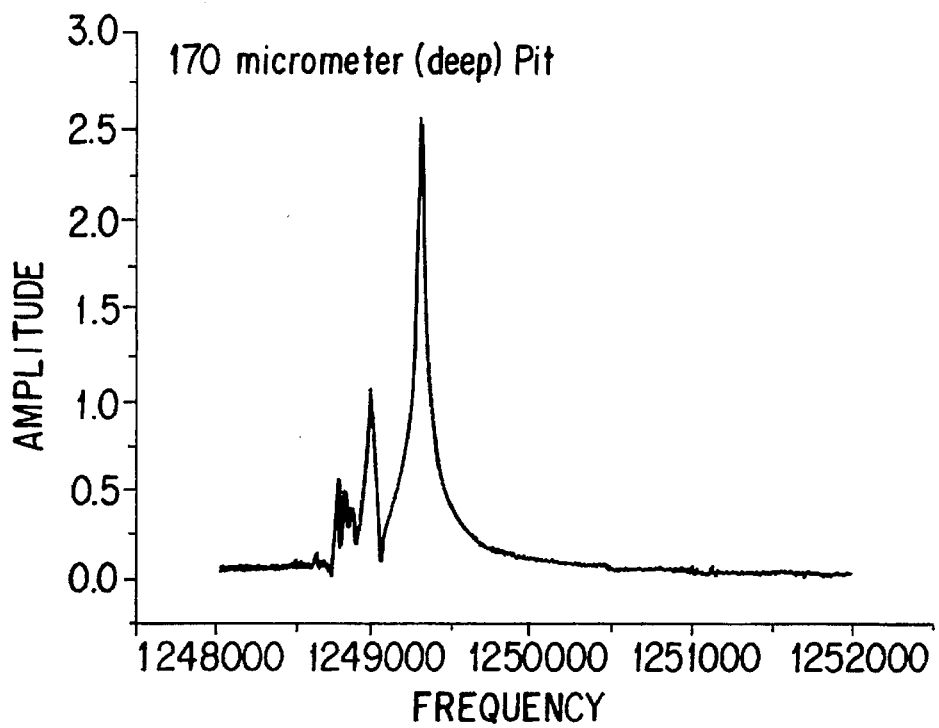
FIG. 3c shows the effect of a 170 um pit in a ball.
Figure 3D:
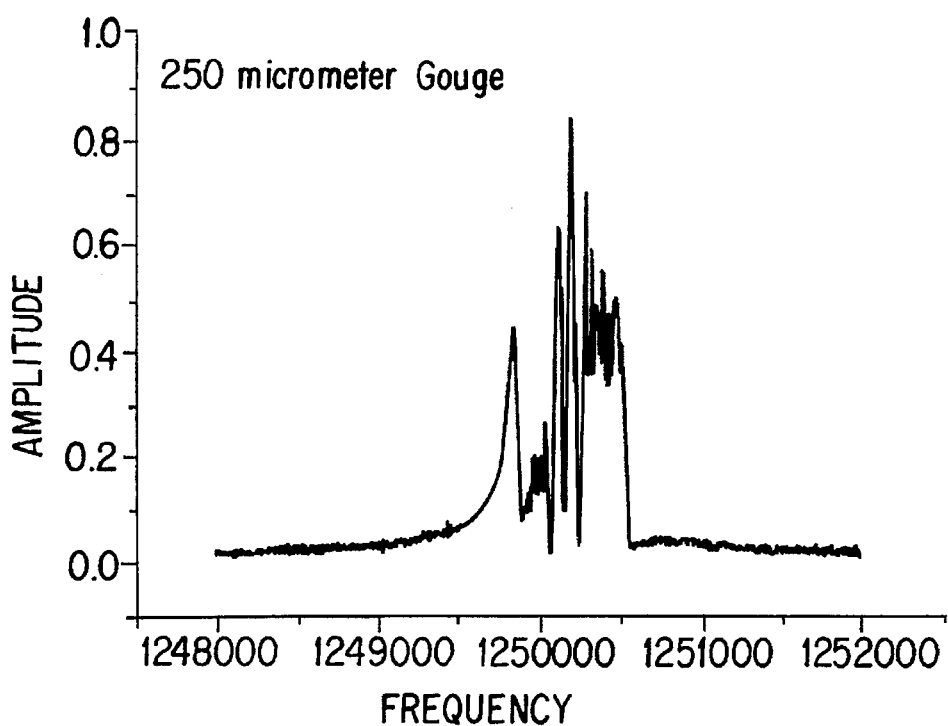
FIG. 3d shows the effect of a 250 micrometer gouge in a ball.
Figure 3E:
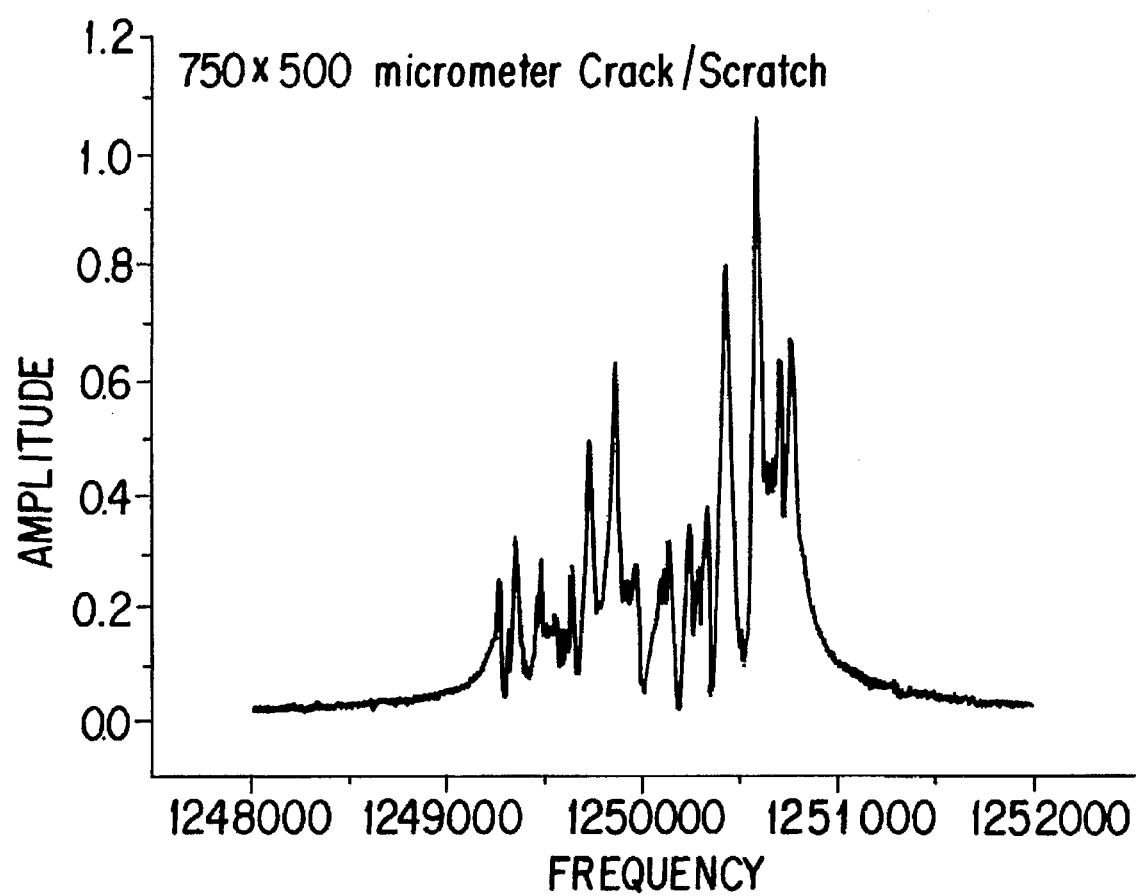
FIG. 3e shows the effect of a 750 by 500 um crack/scratch on a ball.

The plots shown in 3c to 3e illustrate the resonant patterns for several surface flaws which were determined under the microscope. The frequency shift, from the "good" samples is due to a different process for making the $Si_3N_4$ balls used in the test. The shear modulus was slightly different for the two materials, but the modes were the same. These examples show very precise models which predict the frequencies for all resonant modes in a sphere. The defective samples are: FIG. 3c, 170 μm pit; FIG. 3d, 250 μm gouge, and FIG. 3e, 750×500 μm crack/scratch. These examples show that the larger the flaw, the more complex the splitting.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determination of surface conditions in objects comprising the steps of:
   a. mathematically determining degenerate modes which are dependant only upon surface acoustic waves and which have degenerate resonant frequencies;
   b. examining object resonance in at least one frequency region determined to exhibit degeneracy;
   c. observing a deviation from determined degenerate resonances; and
   d. identifying objects which exhibit unacceptale deviations from the mathematically determined degenerate modes.

2. A method according to claim 1, wherein said degenerate modes which are dependant only upon surface acoustic waves are determined by the general equation for a Rayleigh/surface acoustic wave, and wherein said general equation is $$\frac{\partial^2 u}{\partial t^2} - c^2 \Delta u = 0$$

wherein u is a displacement vector of a point on a plane, t is time, and c is the velocity of sound.

3. The method in accordance with claim 2 wherein said general equation becomes $$\frac{\partial^2 u(r,\theta,\phi,t)}{\partial t^2} = c^2 \left[ \frac{1}{r^2} \frac{\partial}{\partial r} \left( r^2 \frac{\partial u}{\partial r} \right) + \frac{1}{r^2 \sin\theta} \frac{\partial}{\partial \theta} \right]$$

when converted to spherical coordinates for surface acoustic wave determination of a ball.

4. A method of detecting surface defects in a ball-shaped test object comprising the steps of:
   a. determining from a wave equation for a sphere, resonant modes which are unique only for surface acoustic waves of said test object;
   b. identifying at least one frequency where a resonant mode unique for only said surface waves exists, for said test object;
   c. applying a plurality of vibrations to said test object where one of said vibrations is at said frequency;
   d. analyzing of resonant amplitude versus said frequency; and
   e. identifying as defective ball-shaped test objects which exhibit a distorted resonant mode where said identified one frequency mode should be observed.

5. The method in accordance with claim 4, wherein said step of identifying includes identifying as defective a part where the single resonant mode is split into a plurality of resonant modes.

6. The method according to claim 4, wherein said wave equation is $$\frac{\partial^2 u}{\partial t^2} - c^2 \Delta u = 0$$

wherein u is a displacement vector of a point on a plane, t is time, and c is the velocity of sound.

7. The method according to claim 6, wherein said wave equation becomes $$\frac{\partial^2 u(r,\theta,\phi,t)}{\partial t^2} = c^2 \left[ \frac{1}{r^2} \frac{\partial}{\partial r} \left( r^2 \frac{\partial u}{\partial r} \right) + \frac{1}{r^2 \sin\theta} \frac{\partial}{\partial \theta} \right]$$

when converted to spherical coordinates for surface acoustic wave determination of a ball.

8. A method for characterizing surface defects of an object by resonant ultrasound spectroscopy comprising the steps of:
   a. identifying by mathematical analysis frequencies at which only surface acoustical waves are generated;
   b. applying to said object acoustic waves having different frequencies, one of which is at said identified only surface acoustic wave frequency;
   c. detecting the resonant response of said object at each of said frequencies; and
   d. determining the presence of a surface defect by comparing the response of a substantially perfect test object to the response of said object.

9. The method in accordance with claim 2 wherein testing is by stepping of a small response interval through a predetermined frequency range.

10. The method according to claim 8, wherein said frequencies at which surface acoustical waves are generated are determined by $$\frac{\partial^2 u}{\partial t^2} - c^2 \Delta u = 0$$

wherein u is a displacement vector of a point on a plane, t is time, and c is the velocity of sound.

11. The method according to claim 10, wherein said frequencies at which surface acoustical waves are generated become determined by $$\frac{\partial^2 u(r,\theta,\phi,t)}{\partial t^2} = c^2 \left[ \frac{1}{r^2} \frac{\partial}{\partial r} \left( r^2 \frac{\partial u}{\partial r} \right) + \frac{1}{r^2 \sin\theta} \frac{\partial}{\partial \theta} \right]$$

when converted to spherical coordinates for surface acoustic wave determination of a ball.

12. A method for testing surface defects of an object comprising the steps of:

a. identifying at least one surface acoustic wave resonant mode for said object;

b. applying a spectrum of vibration frequencies which includes only surface acoustic wave mode frequencies to said object;

c. analyzing response of said object to determine deviation of said response from a known predetermined acceptable objects; and d. accepting or rejecting said object based upon deviation from said one surface acoustic wave resonant mode for said object.

13. The method in accordance with claim 12 wherein said surface acoustic wave resonant frequencies are not responsive to internal characteristics of the part.

14. The method according to claim 12, wherein the step of identifying is in accordance with $$\frac{\partial^2 u}{\partial t^2} - c^2 \Delta u = 0$$

wherein u is a displacement vector of a point on a plane, t is time, and c is the velocity of sound.

15. The method according to claim 14, wherein the step of identifying becomes in accordance with $$\frac{\partial^2 u(r,\theta,\phi,t)}{\partial t^2} = c^2 [\frac{1}{r^2} \frac{\partial}{\partial r} \left( r^2 \frac{\partial u}{\partial r} \right) + \frac{1}{r^2 \sin\theta} \frac{\partial}{\partial \theta}$$

when converted to spherical coordinates for surface acoustic wave determination of a ball.

* * * * *